United States Patent [19]
Reed et al.

[11] Patent Number: 5,098,500
[45] Date of Patent: Mar. 24, 1992

[54] ADHESIVE-FACED POROUS ABSORBENT SHEET AND METHOD OF MAKING SAME

[75] Inventors: Andrew M. Reed; Ian N. Askill, both of Arvada, Colo.

[73] Assignee: PolyMedica Industries, Inc., Woburn, Mass.

[21] Appl. No.: 481,512

[22] Filed: Feb. 15, 1990

Related U.S. Application Data

[62] Division of Ser. No. 150,539, Feb. 1, 1988, Pat. No. 4,906,240.

[51] Int. Cl.$^5$ ............................................. B32B 31/00
[52] U.S. Cl. .................................. 156/253; 156/252; 156/289; 604/304; 604/307
[58] Field of Search ............... 156/289, 252, 253; 128/155, 156; 604/304, 305, 307, 369, 389

[56] References Cited

U.S. PATENT DOCUMENTS

| | | | |
|---|---|---|---|
| 3,547,753 | 12/1970 | Sutton | 156/230 X |
| 3,972,328 | 8/1976 | Chen | 128/156 |
| 4,704,130 | 11/1987 | Gilding et al. | 264/45.5 X |
| 4,726,976 | 2/1988 | Karami et al. | 156/253 X |
| 4,753,231 | 6/1988 | Lang et al. | 128/156 |

Primary Examiner—David A. Simmons
Assistant Examiner—J. Sells

[57] ABSTRACT

A sheet-form material suitable as wound dressing and having enhanced moisture control properties is disclosed. This sheet-form material includes a porous sheet of absorbent, elastomeric segmented polyurethane having an open pore structure and an apertured adhesive facing on one side of the porous sheet. A liquid impermeable but water vapor permeable backing may be provided on the opposite side of the porous sheet, if desired. Also disclosed is a method for forming an apertured adhesive facing for the sheet-form material.

3 Claims, 3 Drawing Sheets

ADHESIVE-FACED POROUS ABSORBENT SHEET AND METHOD OF MAKING SAME

This is a division of application Ser. No. 07/150,539, filed Feb. 1, 1988, now U.S. Pat. No. 4,906,240.

TECHNICAL FIELD

This invention relates to an absorbent sheet and in particular to a polyurethane absorbent sheet suitable as a wound dressing.

BACKGROUND OF THE INVENTION

Wounds produce exudate. The composition of this exudate varies depending upon the nature and location of the wound. While an exudate can be generically characterized as an aqueous mixture of proteinaceous materials, it may also contain blood components, etc., and may serve as a growth medium for bacteria.

In clinical practice, the dressing of wounds has traditionally been accomplished by cleansing the injured area and covering it with absorptive, gauze type materials. In this way the wound is kept "clean and dry" throughout the duration of its healing process.

However, there has been increasing acceptance of the view that for optimal wound healing to occur from the standpoint of rate of healing, quality of healing, etc., a moist microenvironment around the wound is preferential as opposed to the "clean and dry" approach. As this acceptance of the moist wound healing theory has grown, wound dressings promoting a moist wound microenvironment have entered the marketplace.

The control of exudate is of prime importance if a moist wound microenvironment is to be maintained. It can be appreciated that if a dressing removes all the exudate that a wound produces, a "dry" wound results which is suboptimal for wound healing. Similarly, if the dressing does not control the level of exudate sufficiently, then an excess "pool" of material develops which may subsequently leak thus soiling clothing and bed linen, and breaching any barrier to bacterial infection.

Ideally, a wound dressing must be adhesive in nature such that it may attach to the wound site. The adhesive utilized must be biocompatible, non-cytotoxic and free of toxic leachable substances as well as have the desired balance of physical properties such as moisture vapor transport rate, tack, long term adhesion properties, etc. Inasmuch as in use the adhesive will be in direct contact with the wound site and surrounding intact area, it must be non-toxic and should elicit no more than a minimal allergenic response.

Additionally, a wound dressing should possess the ability to prevent bacteria from entering the wound from the ambient environment while providing the proper moisture vapor transport rate.

Other aspects such as a dressing's ability to conform to irregular contours of the body are also desirable. This may be accomplished by utilizing elastomeric, flexible, polymeric materials in the construction of the dressing.

Having outlined the major desirable design characteristics of environmental wound dressings it is beneficial to examine the mode of operation of existing wound dressings to appreciate their deficiencies.

Environmental dressings, i.e., dressings which maintain a beneficial microenvironment around a wound, can be categorized into three broad classes: hydrocolloid/gel dressings; film dressings; and foam dressings. These dressings maintain specific microenvironments, e.g., moisture, temperature, gaseous transport, etc., around a wound by utilizing a variety of physical mechanisms.

Hydrocolloid type dressings as described in U.S. Pat. No. 4,477,325 to Osburn are relatively thick and as a result possess low conformability. The mode of exudate control is by absolute absorption by a gel (hydrocolloid) in the dressing. The ability for moisture to pass through the dressing to the external environment is minimal. On highly exuding wounds the dressing's absorption capacity can be exceeded which leads to leakage and subsequent disruption of the bacterial barrier. Some hydrocolloid compositions dissolve and fall into the wound bed thus requiring time consuming cleaning, which disrupts the wound site, at subsequent dressing changes.

The ability of a film dressing to transport moisture is a function of film thickness and chemical composition. On moderate to high exuding wounds, exudate tends to collect under film dressings and form "pools". This collection of exudate indicates that current polymer film dressings have a moisture vapor transmission rate which is too low to handle the exudate from many wounds. It has been suggested that the "pool" of exudate may increase the risk of bacterial proliferation leading to infection. Similarly, if the "pool" reaches excessive proportions leakage will occur thus breaking the bacterial barrier.

Polymer film dressings as described in U.S. Pat. No. 3,645,835 to Hodgson and U.S. Pat. No. 4,513,739 to Johns are thin and possess high conformability. The wound contacting surfaces are coated with pressure sensitive adhesives carried on the film. The films that are used are liquid impermeable polyurethane elastomers. Thus wound exudate is not allowed to ingress into the film. The sole mode of exudate control is by allowing vapor of the aqueous portion of the exudate to permeate into the polymer film from where it diffuses into the external environment. As the moisture vapor permeability is low, the polymer film's absolute absorption capacity is also low especially when compared to hydrocolloid dressings.

Foam dressings also manage exudate by evaporation of the aqueous portion of the exudate through the dressing to the surrounding environment. Control of this moisture vapor transmission rate is a function of the chemical composition of the foam coupled with the pore structure. Due to their gross pore sizes, foam dressings tend to desiccate wounds resulting in dressings which become brittle and nonconformable during use. These hardened dressings often traumatize the underlying healing wound bed. Furthermore, either special processing and/or a wetting agent is required to make the foam hydrophilic.

Dependent upon the type of foam structure used, exudate is also managed by capillary action into the pores of the structure. Most foam structures used as dressings contain interconnecting pores and thus provide limited bacterial barrier properties because the mean pore diameter exceeds the dimensions of many bacteria. Similarly, such dressings contain pore sizes which are sufficiently large as to fall into the range of sizes into which regenerating tissue will grow. As a result of this, ingrowth of tissue into the dressing's structure occurs thus impeding removal of the dressing and traumatizing the wound site.

Open cell foam dressings are described in U.S. Pat. No. 3,975,567 to Lock and U.S. Pat. No. 3,978,855 to McRae et al. The foam is made hydrophilic by permanently compressing the cells of the microporous foam to form a microporous skin which contacts the wound site. Thus these patents teach against larger pores contacting the wound site and smaller pores away from the wound site as is taught by the present invention. Also, a wetting agent is added to enhance absorption of exudate into the porous structure.

An example of a foam dressing with pores into which regenerating tissue grows is U.S. Pat. No. 3,949,742 to Nowakowski. In this particular invention a thrombogenic open cell reticulated foam is used laminated to a non-porous polyurethane film. The dressing provides a matrix into which fibroblasts and new capillaries can grow. Thus the wound site is traumatized by removal of the dressing.

The present invention maintains the desired level of moisture, temperature and gaseous exchange at the wound site. By the control of these properties, the microenvironment thus produced is the optimal required for healing of the wound. At the same time, the present invention manages exudate, is adhesive, biocompatible, non-toxic, conformable, elastomeric and also provides a bacterial barrier.

SUMMARY OF THE INVENTION

The present invention contemplates an adhesive-faced absorbent sheet well suited for making a wound dressing which enhances the healing of a wound by providing about the wound a microenvironment that promotes healing. A method of manufacturing the absorbent sheet is also contemplated.

The adhesive-faced sheet of this invention is an absorbent, elastomeric, porous polyurethane sheet provided with an apertured adhesive facing on one side of the porous sheet. For use as a wound dressing, an optional polyurethane sheet or film may be provided as a backing for the porous polyurethane sheet. The polyurethane preferably is a segmented polyurethane.

More particularly, the present wound dressing comprises an adhesive-faced porous sheet of absorbent, elastomeric, polyurethane having an open pore structure and defining macropores at one surface of the porous sheet. The adhesive facing for the porous sheet is provided contiguous with the macropore containing surface and defines apertures that communicate with the macropore and provide fluid channels to the macropore and thus to the interior of the porous sheet.

The wound dressings of the present invention control exudate and moisture level at the wound site by controlling the absolute absorption and moisture vapor transport rate of the exudate. These parameters are adjusted by modifying the chemical composition of the polyurethane used to make the porous sheet, the porous structure of the sheet, and the composition and thickness of the apertured adhesive facing. Thus a series of wound dressings which provide a continuum of different microenvironments is provided. These dressings can be designed to suit particular wound types, e.g., ulcers, donor sites, burns, high exuding and low exuding wounds, etc. They are easy to use and maintain the desired microenvironment to attain optimal wound healing.

A method of forming the wound dressing having an apertured adhesive facing is also disclosed. According to this method, the porous, elastomeric segmented polyurethane sheet and a viscous sheet-form adhesive layer are juxtaposed, and then the porous polyurethane sheet is compressed against the adhesive layer for a relatively short time period, e.g., by passing a roller over the surface of the porous sheet opposite from the surface in contact with the adhesive layer. Upon release of the applied compressive force, the elastomeric porous sheet springs back to its previous configuration while generating apertures in the adhesive layer contiguous therewith. After the foregoing treatment, the adhesive layer remains as an apertured adhesive facing on the porous polyurethane sheet.

Numerous other advantages and features of the present invention will become readily apparent from the following detailed description of the invention, the accompanying examples, drawings and the appended claims.

DETAILED DESCRIPTION OF THE PREFERRED EMBODIMENTS

While this invention is susceptible to embodiment in many different forms, preferred embodiments of the invention are shown and described in this specification. It should be understood, however, that the present disclosure is to be considered as an exemplification of the principles of this invention and is not intended to limit the invention to the embodiments illustrated.

Figure 1:
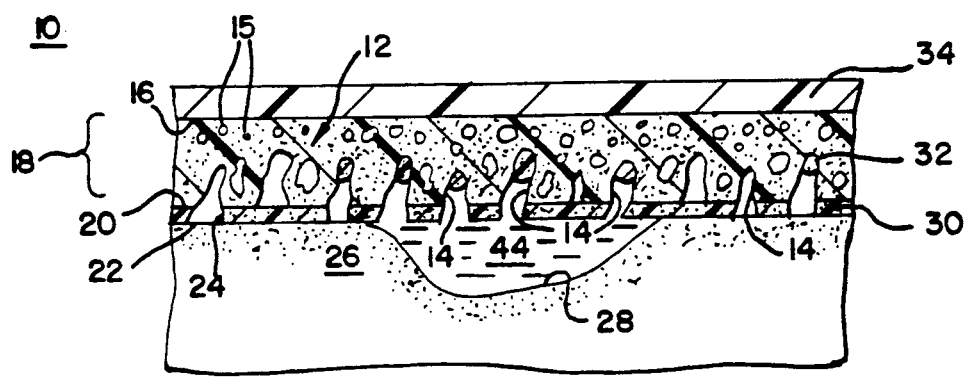
FIG. 1 is a fragmentary sectional view of an absorbent wound dressing embodying the present invention as applied to a wound site.

As shown in FIG. 1, the wound dressing 10 of the present invention includes an absorbent porous sheet or layer 12 which is capable of absorbing exudate 44 from a wound bed 28 of a wound site 26. Preferably, micropores as well as macropores are present in sheet 12. In the embodiment shown in FIG. 1, macropores 14 and micropores 15 in the porous sheet 12 provide a pore size gradient 18 of decreasing pore size across the thickness of sheet 12, i.e., from a first or bottom face 20 to a second or top face 16. Openings 22 in bottom face 20 are formed by macropores 14 that extend to the surface of sheet 12. An adhesive layer 30 on first face 20 provides an adhesive facing for the wound dressing 10. Apertures 24 in the adhesive layer 30 are formed by the repositioning of adhesive portions or fragments 32 of the adhesive layer 30 to the interior of macropores 14 as will be described in greater detail hereinbelow.

An optional hydrophilic backing layer 34 is provided on the second face 16 as a backing for the wound dressing 10. Hydrophilic layer 34 is useful to further modulate the rate of vapor transmittal through the dressing and thus aids in maintaining the proper moisture content at the wound site 26 during the healing process.

The absorbent microporous layer utilized herein is a biocompatible hydrophilic polyurethane or the like.

Preferred for the present wound dressings are segmented polyurethanes of the type disclosed in U.S. Pat. No. 4,704,130 to Gilding et al and in U.S. Pat. No. 3,635,907 to Schulze et al. Other suitable materials are polyurethanes derived from polyethylene glycol linked with glycerol and toluene diisocyanate or methylene diisocyanate, e.g., the Hypol ™ type materials commercially available from W. R. Grace & Co.

The porous nature and a desired pore size gradient in the absorbent porous layer can be achieved by a controlled precipitation process as described in U.S. Pat. No. 4,704,130 to Gilding et al. Utilizing that process, the structure, pore size distribution and pore size gradient of the porous layer can be altered by adjusting any or all of the following variables:

(a) Percent polymer in solution—increasing the solids content of the polymer solution increases the viscosity of the solution and decreases the pore size of the resultant porous layer.

(b) Molecular weight of the polymer in solution—increasing the molecular weight of the polymer in solution will decrease the size of the pore of the resultant porous layer.

(c) Solvent/non-solvent ratio of the polymer solution—decreasing the solvating power of the solvent or solvent/non-solvent in which the polymer is dissolved will result in a porous layer with smaller pores.

(d) Temperature of the polymer solution—increasing the temperature of the polymer solution will increase the relative solubility of the polymer and lead to increased porous layer porosity.

(e) Type of non-solvent in precipitation bath—choice of non-solvents whose solubility parameters indicate that they are almost solvents for polyurethane will result in a porous layer with larger pores. Use of non-solvents whose solubility parameters indicate that they are far from being solvents will result in a porous layer with smaller pores.

(f) Solvent/non-solvent ratio in the percipitation bath—as in (e) above, the solubility parameters of the mixture will determine pore size, i.e., if the mixture is close to being a solvent large pores will be produced and if the mixture is far from being a solvent small pores will be produced.

(g) Temperature of the precipitation bath —the higher the temperature of the precipitation bath the more open the pore structure of the resulting porous layer.

(h) The rate of immersion of the polymer solution into the precipitation bath—the faster the immersion, the tighter the pore structure of the resultant porous layer.

The adhesive layer for the adhesive facing of the present wound dressing is compounded to be non-cytotoxic and non-allergenic when used on patients. The adhesive properties of the facing are selected to give the desired degree of bioadhesion, tack, etc., while maintaining the desired level of hydrophilicity and moisture transport. The adhesive properties of the adhesive layer are adjusted so that the cohesive strength of the adhesive is less than the adhesive strength of the adhesive to the porous sheet, and further so that the adhesive strength vis-a-vis the porous sheet is greater than that vis-a-vis the tissue in contact with the adhesive. In addition, the elastic modulus of the porous sheet is higher than the ultimate tensile strength of the adhesive layer. The cohesive strength of the adhesive also is less than the tensile strength of the porous sheet. The adhesive facing usually is about 0.0002 to about 0.001 inches (about 5 to about 25 microns) thick, preferably about 0.0005 inches (about 12.5 microns) thick.

Preferably, the adhesive is a visco-elastic, acrylic-based pressure sensitive adhesive constituted by copolymers of 2-ethylhexyl acrylate and acrylic acid having a tensile strength of no more than about 2.5 grams per square millimeter at a strain rate of 25 times the sample length per minute. The amount of acrylic acid present usually is in the range of about 10 to about 25 mol-percent, preferably about 12 to about 17 mol-percent.

The acrylic-based pressure sensitive adhesive as a 40 weight percent solution in ethyl acetate preferably has a viscosity of no more than about 15,000 centipoises at about room temperature, more preferably a viscosity in the range of about 500 to about 8,000 centipoises.

Other suitable pressure sensitive adhesive compositions are described in U.S. Pat. No. 3,645,835 to Hodgson.

The outer hydrophilic layer or backing is preferably made from a solvent cast polyurethane as a thin film. This film is liquid impermeable but water vapor permeable. By varying the chemical composition, the moisture vapor transmission rate (MVTR) of the film can be adjusted as desired. Due to the nature of the outer hydrophilic backing, bacterial barrier properties for the present wound dressings are obtained as well. The preferred nominal thickness of this layer is approximately 0.002 inches (0.005 cm).

The present wound dressing is packaged in sterile heat sealable pouches with the adhesive facing protected by a release sheet. The preferred sterilization method is by gamma irradiation. However, steam autoclaving or ethylene oxide treatment may be utilized.

Although the preferred form of the present wound dressing includes three layers, as pointed out hereinbefore the backing may be omitted.

Figure 2:
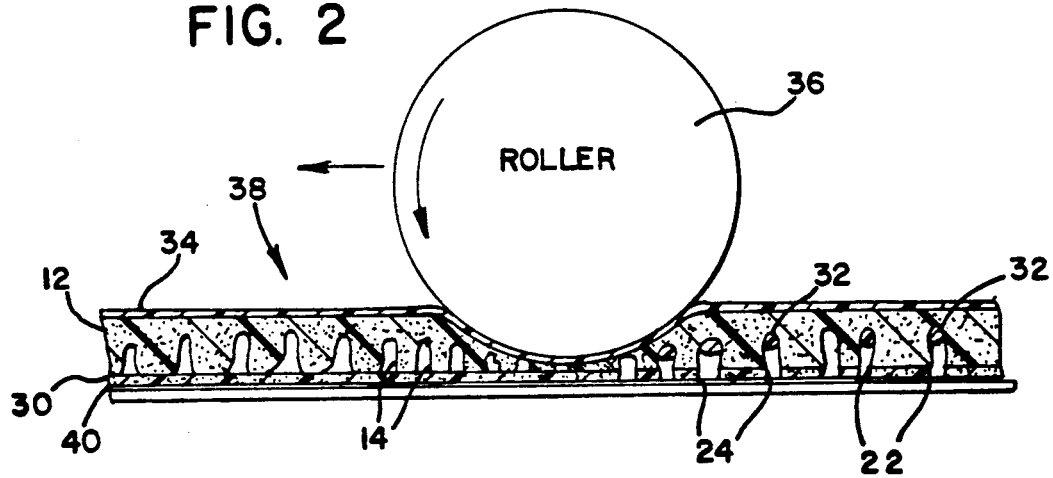
FIG. 2 is a sectional view of a method for forming apertures in the adhesive facing of the present wound dressing.

A method for producing an apertured adhesive facing is shown in FIG. 2. First, a laminate 38 is produced by juxtaposing porous absorbent sheet 12 and adhesive layer 30. Next a force is applied to the laminate 38 so as to compress sheet 12 against adhesive layer 30. While FIG. 2 discloses a roller 36 as applying the desired compressive force, other known suitable means to achieve compression are acceptable. The applied force urges portions of the inner surface of pores 14 in contact with the adhesive layer 30 through openings 22. Subsequent removal of the applied force allows the absorbent porous sheet 12 to substantially return to its pre-compression configuration. However, a portion of the adhesive in contact with the inner surfaces of macropores 14 is retained thereon, thereby producing apertures or holes 24 in the adhesive facing in registry with macropores 14. The apertures 24, in turn, provide fluid access to the interior of sheet 12.

Figure 3:
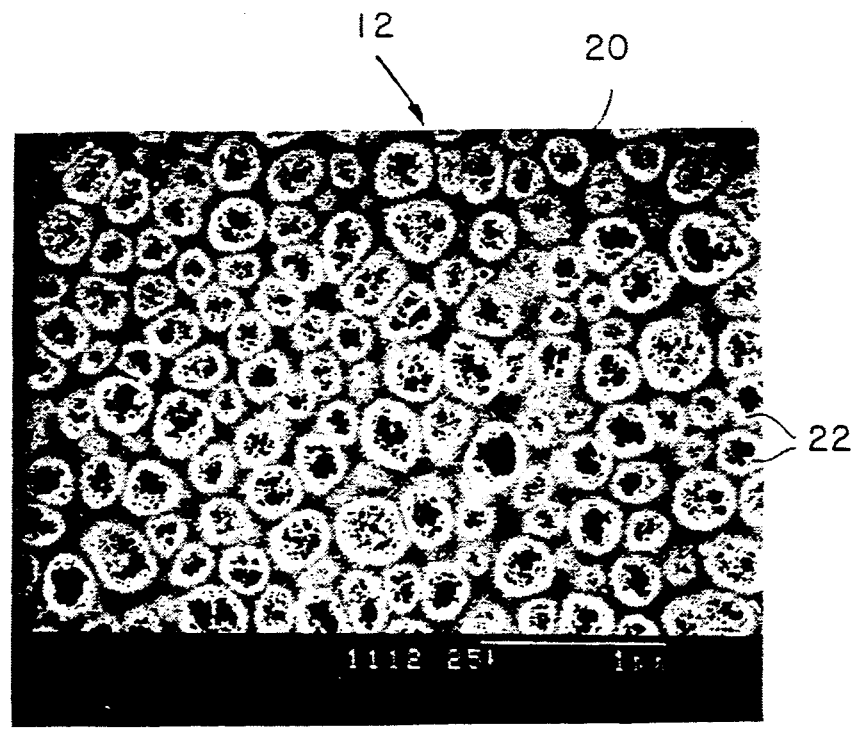
FIG. 3 is a micrograph illustrating macropores on the surface of the porous segmented polyurethane sheet.
Figure 4:
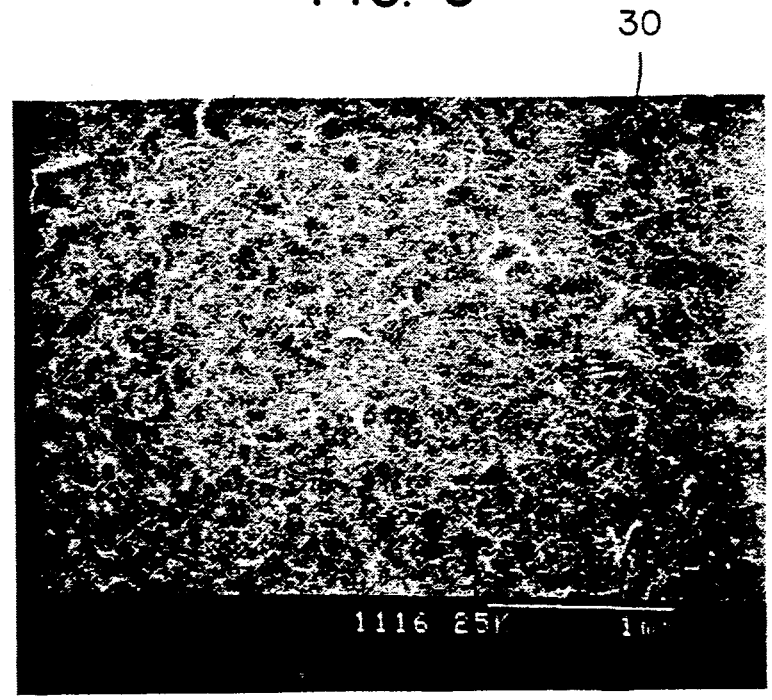
FIG. 4 is a micrograph illustrating an adhesive layer as applied to the porous segmented polyurethane sheet but before formation of apertures therein.
Figure 5:
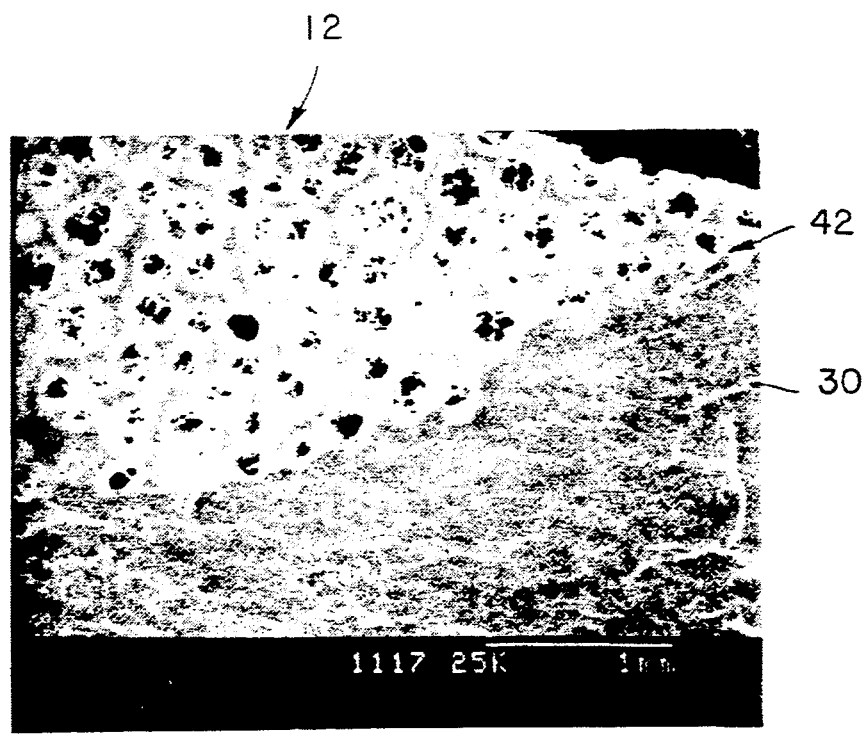
FIG. 5 is a micrograph illustrating the interface between the porous segmented polyurethane sheet and the adhesive facing contiguous therewith.
Figure 6:
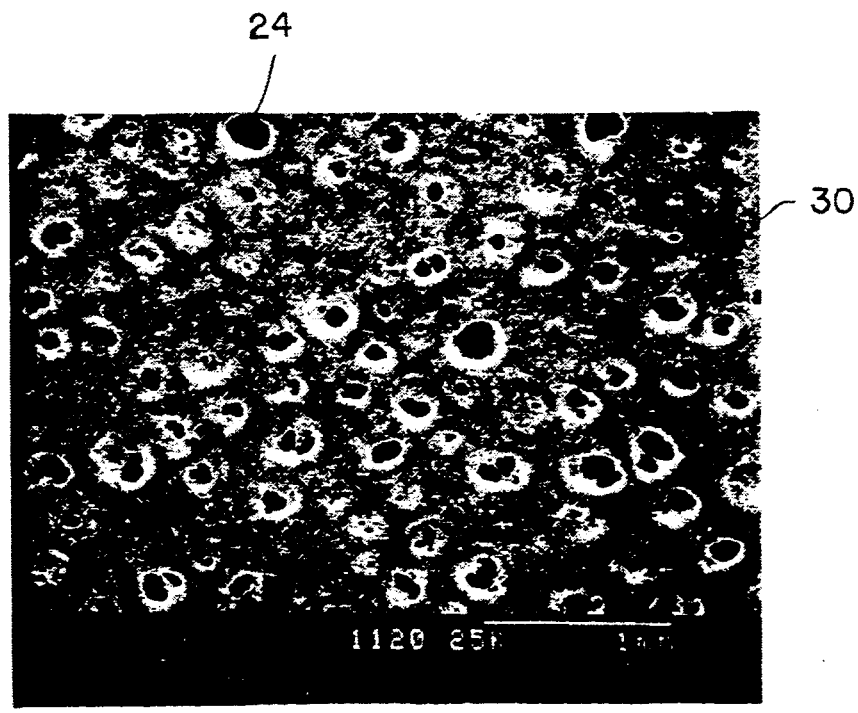
FIG. 6 is a micrograph illustrating apertures in the adhesive facing of the present wound dressing.

FIGS. 3–6 are scanning electron micrographs at 30× magnification of a wound dressing made in the foregoing manner. In particular, FIG. 3 shows an absorbent sheet surface 20 of the porous layer 12 before application of the adhesive layer. Openings 22 are defined by macropores that extend to the surface of the porous sheet. FIG. 4 shows the adhesive layer 30 as applied to the porous sheet before the latter is compressed. FIG. 5 shows the underlying microporous layer 12 and the edge 42 of the adhesive layer 30. Finally, FIG. 6 shows the apertured adhesive facing derived from the applied adhesive layer 30 after application of the compressive force to the porous layer. The aperture density was about 8.6% as measured by computer digitization.

As illustrated in FIGS. 5 and 6, not all of the openings 22 of the microporous sheet 12 result in apertures 24 in the adhesive layer 30. However, that is not required. For effective exudate transport through the adhesive layer 30, minimum aperture surface density in the adhesive facing can be as low as about 1 to about 2%. The preferred surface aperture density in the adhesive facing is about 5 to about 15%. The surface aperture density can be as high as about 25%.

While not wishing to be bound by a particular mechanism of operation, the present invention is believed to function as a wound dressing in the following manner.

The dressing is placed onto a wound site with the adhesive side toward the wound bed. The pressure sensitive adhesive adheres to the intact skin around the wound bed. Similarly, it is believed that the adhesive adheres initially to the moisture exuding wound bed as well as to the surrounding region. Over a period of time the adhesive contacting the wound bed may hydrate such that it is no longer firmly adhered to the wound. The dressing, however, is maintained in close apposition to the wound bed by the capillary action of the exudate entering the microporous substructure of the dressing. Due to the designed level of moisture vapor transmission rate (MVTR) and controlled discontinuities, i.e. the apertures, in the adhesive layer, proteinaceous exudate passes into the porous structure of the absorbent microporous layer of the dressing.

The level of hydrophilicity of the microporous layer and pore architecture are designed such that surface tension is minimized to allow the easy passage of exudate into the pores. The exudate is retained in the dressing's pore structure while maintaining a high relative humidity at the wound site. The pore size of the porous sheet of the dressing can be controlled to provide a matrix into which regenerating tissue cannot grow, if desired.

When a backing is provided over the exudate-retaining sheet of the dressing, further control of the loss of the aqueous portion of the exudate by evaporation is possible. In this manner a balance between moisture loss and exudate uptake may be attained while maintaining a moist wound microenvironment.

The following examples illustrate typical processes and compositions for practicing the present invention, but are not to be construed as limitations thereof. In these examples, certain materials are referred to by their commercial names in the interest of brevity. These materials are:

Mitrathane TM M1020—a segmented polyetherurethane-urea derived from diphenylmethane diisocyanate, polytetramethylene glycol having a number average molecular weight of about 1,000, and organic amines in an amount sufficient to provide for about 20-fold chain extension;

Mitrathane TM M2007—a segmented polyetherurethane-urea derived from diphenylmethane diisocyanate, polytetramethylene glycol having a number average molecular weight of about 2,000, and organic amines in an amount sufficient to provide for about 7-fold chain extension; and Mitrathane TM MPU-5—a segmented polyetherurethane-urea derived from diphenylmethane diisocyanate, polytetramethylene glycol, polyethylene glycol, and organic amines as chain extenders.

All of the above materials are commercially available from Matrix Medica, Inc., Wheat Ridge, Colo.

EXAMPLE 1

Manufacture of Absorbent Sheet

The porous layer of the present invention is manufactured from a segmented polyurethane such as Mitrathane TM M1020. The material is supplied as a 25 weight percent solids solution in dimethylacetamide (DMAC). To this Mitrathane TM solution a solution of polyvinylpyrollidone (PVP) (M.W. 360,000) in DMAC is added such that the total solids of the mixture is 15 weight percent in DMAC (12% Mitrathane TM M1020; 3% PVP). The resulting viscosity of the produced mixture at 21° C. is within the range of about 1,500–2,500 cp as measured using a Brookfield viscometer. This mixture is cast onto a substrate to a nominal thickness of about 0.05 inches. By known methods, such as described in U.S. Pat. No. 4,704,130 to Gilding et al., the substrate and cast solution are immersed in a water bath at about 15° to about 25 ° C. The polymer precipitates out of solution while in the water bath. The time elapsed in the water bath is between about 5 to about 30 minutes. The porous sheet thus formed is dried, while being constrained, at about 45° to about 55° C. for about two hours in a forced hot air oven.

The structure of the produced sheet includes one surface with pores in the range of about 0.1 to about 1 micron as revealed by a scanning electron microscope (SEM). Under this surface lie "finger-like" voids or macropores having dimensions of approximately 20 microns across by approximately 750 microns deep. These voids extend to the other surface of the formed sheet and define therein fluid access openings.

The thus formed porous sheet has the following physical properties: tensile strength to break—0.09 kg/mm$^2$; elongation at break—326%; Moisture Vapor Transmission Rate (MVTR), measured by the modified ASTM Test No. E-96-80 using an inverted cup at 37° C.—25,000 g/m$^2$/24 hrs; water absorption—500%.

EXAMPLE 2

Manufacture of Adhesive Layer

The adhesive is formulated to be hydrophilic and consists essentially of a biocompatible copolymer of 2-ethylhexyl acrylate and acrylic acid containing about 15 mol-% of the latter. It is supplied as a 40% solids solution in ethyl acetate. The solution of adhesive is spread onto a release paper to obtain a uniform coating. The release paper and adhesive layer are placed in a forced hot air oven at approximately 45 to approximately 55° C. for about 2 hours to remove residual solvent. The adhesive layer is cast such that a final adhesive coating weight of approximately 12 g/m$^2$ is obtained.

EXAMPLE 3

Manufacture of Backing Sheet

The outer polyurethane layer is prepared from a polyurethane such as Mitrathane TM MPU-5. The material is supplied as a 25 weight percent solids solution in dimethylacetamide (DMAC). This solution is spread to the desired thickness on a glass plate and the solvent removed by heating to a temperature in the range of about 50° to about 70° C. for approximately 2 hours.

The properties of the backing sheet produced as described above are typically: tensile strength at break—5.35 kg/mm$^2$; elongation at break—990%; thickness—0.002 inches; MVTR—8,100 g/m$^2$/24 hrs.

EXAMPLE 4

Assembly of Wound Dressing

To construct the absorbent wound dressing, the respective sheets and layers produced in accordance with Examples 1-3, above, are assembled as follows:

The polyurethane backing is coated with a thin layer of an aprotic solvent such as dimethylacetamide (DMAC), dimethylformamide (DMF) or dimethylsulphoxide (DMSO). The solvent of choice is DMSO. Alternatively, a thin layer of the hydrophilic polyurethane dissolved in a solvent can be utilized as an adhesive. The backing is placed onto the surface face of the porous polyurethane sheet free from macropores. Pressure is applied to the composite to minimize air entrapment at the interface. The resulting structure is placed in a forced hot air oven for about 25 to about 35 minutes at about 65° to about 75° C. This heat treatment removes any bonding solvent that may be present.

Subsequently, the macropore-containing face of the porous layer is contacted with the preformed pressure sensitive adhesive layer. Bonding is achieved by applying heat and/or pressure to the resulting composite.

The sheet-form composite is then subjected to a compressive force to form apertures in the adhesive layer.

The completed sheet-form composite is cut to the desired size and shape, packaged in medical heat sealable pouches and sterilized.

This sheet-form composite embodying the present invention has the following physical characteristics: tensile strength to break—0.18 kg/mm$^2$; elongation at break—630%; thickness—0.026 inches; water absorption—225%; MVTR—6,900 g/m$^2$/24 hrs.

EXAMPLE 5

Manufacture of Wound Dressing Without Backing

The porous layer and the adhesive layer are formed as disclosed in Examples 1 and 2, above. The porous layer and the adhesive layer are then bonded together and further processing is done as described in Example 4, above.

This produced sheet-form material has the following properties: tensile strength to break—0.09 kg/mm$^2$; elongation at break—326%; thickness—0.03 inches; water absorption—500%; MVTR—24,000 g/m$^2$/24 hrs.

EXAMPLE 6

Manufacture of Wound Dressing Without Backing

The porous layer of this example is fabricated from Mitrathane TM M2007, a segmented polyetherurethane-urea. The material is supplied as a 25 weight percent solids solution in dimethylacetamide (DMAC). To this Mitrathane TM solution a solution of polyvinylpyrollidone (PVP; M.W. 360,000) in DMAC is added such that the total solids of the mixture is 17 weight percent in DMAC (15% Mitrathane TM M2007, 3% PVP). The resulting polymer solution is then processed as described in Example 1, above, into a porous sheet. A wound dressing is then fabricated as described in Example 5, above.

The resulting sheet-form material has the following physical characteristics: tensile strength to break—0.17 kg/mm$^2$; elongation at break—500%; thickness—0.02 inches; water absorption—190%; MVTR—9,800 g/m$^2$/24 hrs.

EXAMPLE 7

Manufacture of Wound Dressing Without Backing

The porous layer is made from Mitrathane TM M2007, a polyetherurethane-urea by the process described in Example 1, above. A wound dressing is then fabricated as described in Example 5, above.

The resulting wound dressing has the following physical characteristics: tensile strength to break—0.32 kg/mm$^2$; elongation at break—450%; thickness—0.017 inches; water absorption—250%; MVTR—1,370 g/m$^2$/24 hrs.

This invention has been described in terms of specific embodiments that have been set forth in detail. It should be understood however, that these embodiments are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

We claim:

1. A process for manufacturing an adhesive-faced, sheet-form absorbent material suitable as a wound or burn dressing, surgical drape or the like wherein said adhesive facing is apertured, which process comprises the following steps:
    providing an elastomeric, absorbent, porous sheet said porous sheet having an open pore structure and defining macropores on one surface of said macroporous sheet;
    providing an adhesive layer as a viscous mass on a release surface said adhesive layer having a cohesive strength less than the adhesive strength of the adhesive to the porous sheet;
    juxtaposing said porous sheet and said adhesive layer such that said adhesive layer is contiguous with the macropore-containing surface of said porous sheet;
    compressing said juxtaposed porous sheet and adhesive layer; and
    removing said applied compressive force from a resulting laminate so that when said porous sheet springs back to its previous configuration portions of the adhesive layer bond to at least some of the surfaces of the macropores of the porous sheet forming apertures in said adhesive layer.

2. The process of claim 1 further comprising the step of securing a liquid impermeable but water vapor permeable backing sheet to the sheet-form absorbent material.

3. The process of claim 1 wherein said porous sheet is a segmented polyurethane.

* * * * *